United States Patent
Xu et al.

(12) 
(10) Patent No.: US 11,746,080 B2
(45) Date of Patent: Sep. 5, 2023

(54) METHODS OF REDUCING COLOR IN ALKANOLAMINE COMPOSITIONS AND COMPOSITIONS PRODUCED THEREBY

(71) Applicant: SABIC Global Technologies B.V., Bergen Op Zoom (NL)

(72) Inventors: Feng Xu, Riyadh (SA); Flaiyh Al-Anazi, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/809,910

(22) Filed: Mar. 5, 2020

(65) Prior Publication Data

US 2020/0199061 A1 Jun. 25, 2020

Related U.S. Application Data

(62) Division of application No. 16/060,309, filed as application No. PCT/IB2016/057384 on Dec. 6, 2016, now Pat. No. 10,662,144.

(60) Provisional application No. 62/266,163, filed on Dec. 11, 2015.

(51) Int. Cl.
| | | |
|---|---|---|
| C07C 213/10 | (2006.01) | |
| C07F 5/02 | (2006.01) | |
| C07D 215/08 | (2006.01) | |
| C07D 215/10 | (2006.01) | |
| C07D 215/12 | (2006.01) | |

(52) U.S. Cl.
CPC ............ *C07C 213/10* (2013.01); *C07F 5/022* (2013.01); *C07F 5/027* (2013.01); *C07D 215/08* (2013.01); *C07D 215/10* (2013.01); *C07D 215/12* (2013.01)

(58) Field of Classification Search
None
See application file for complete search history.

(56) References Cited

U.S. PATENT DOCUMENTS

| | | |
|---|---|---|
| 2,901,513 A | 8/1959 | Thomas |
| 3,207,790 A | 9/1965 | Glew et al. |
| 3,453,183 A | 7/1969 | Okubo et al. |
| 3,742,059 A | 6/1973 | Dowd |
| 3,819,710 A | 6/1974 | Jordan |
| 4,567,303 A | 1/1986 | Boettger et al. |
| 4,673,762 A | 6/1987 | Paslean et al. |
| 4,877,450 A | 10/1989 | Brasch |
| 5,197,996 A | 3/1993 | Reid et al. |
| 5,604,275 A | 2/1997 | Zhong et al. |
| 5,693,866 A | 12/1997 | Roling et al. |
| 5,847,221 A | 12/1998 | Gibson |
| 6,291,715 B1 | 9/2001 | Ruider et al. |
| 7,425,652 B2 | 9/2008 | Wang et al. |
| 7,560,594 B2 | 7/2009 | Haese et al. |
| 8,466,323 B2 | 6/2013 | Melder et al. |
| 2004/0127748 A1 | 7/2004 | Brun-Buisson et al. |
| 2004/0158102 A1 | 8/2004 | Morishita et al. |
| 2006/0142615 A1 | 6/2006 | Brun-Buisson et al. |
| 2007/0027056 A1 | 2/2007 | Wang et al. |
| 2007/0276161 A1 | 11/2007 | Hollmann et al. |
| 2014/0061020 A1 | 3/2014 | Schmidt et al. |

FOREIGN PATENT DOCUMENTS

| | | |
|---|---|---|
| CA | 2061718 A1 | 11/1992 |
| CA | 2540246 A1 | 4/2005 |
| CN | 1140163 A | 1/1997 |
| CN | 1329588 A | 1/2002 |
| CN | 201524433 | 7/2010 |
| EP | 0004015 A1 | 2/1979 |
| EP | 1132371 A1 | 3/2001 |
| EP | 1791805 B1 | 8/2005 |
| EP | 2177501 A1 | 4/2010 |
| GB | 1363994 | 8/1974 |
| RU | 2430085 C1 | 9/2011 |
| WO | WO0032553 A1 | 6/2000 |
| WO | WO03048105 A1 | 6/2003 |
| WO | WO2005058795 A1 | 6/2005 |

OTHER PUBLICATIONS

Goralski et al. "Hydroboration. 81. Synthesis of 2-(dialkylamino)boronic esters and acids via hydroboration of enamines. A convenient preparation of .beta.-dialkylamino alcohols." The Journal of Organic Chemistry, American Chemical Society Etc., vol. 52, Jan. 1, 1987, pp. 4014-4019, XP002694238, ISSN: 0022-3263, DOI: 10.1021/J000227A014.

International Preliminary Report on Patentability; International Application No. PCT/IB2016/057384; International Filing Date Dec. 6, 2016; dated Jun. 12, 2018, 6 pages.

International search Report and Written Opinion from PCT/IB2016/057384 dated Mar. 21, 2017, 11 pages.

*Primary Examiner* — Sudhakar Katakam
*Assistant Examiner* — Jennifer C Sawyer
(74) *Attorney, Agent, or Firm* — Norton Rose Fulbright US LLP

(57) ABSTRACT

A method of reducing color in an alkanolamine is described. The method includes contacting the alkanolamine with a color-reducing amount of a borane complex effective to provide a color-reduced alkanolamine composition having a Platinum-Cobalt Color Value, according to Test Method ASTM D1209, of less than 50.

10 Claims, No Drawings

METHODS OF REDUCING COLOR IN ALKANOLAMINE COMPOSITIONS AND COMPOSITIONS PRODUCED THEREBY

CROSS-REFERENCE TO RELATED APPLICATIONS

This application is a divisional of U.S. application Ser. No. 16/060,309, which is a national phase application under 35 U.S.C. § 371 of International Application No. PCT/IB2016/057384 filed Dec. 6, 2016, which claims priority to United States Provisional Patent Application No. 62/266,163 filed Dec. 11, 2015. The entire contents of each of the above-referenced disclosures is specifically incorporated by reference herein without disclaimer.

BACKGROUND

This disclosure relates to methods of reducing color in alkanolamine compositions and the reduced-color compositions produced thereby.

Alkanolamines such as triethanolamine are used primarily as emulsifiers and surfactants in a wide variety of industrial and consumer product applications. Such applications include household goods, for example dishwashing liquids, detergents, cleaners, polishes, cement production, cosmetics such as personal care products including shaving creams, medicine, printing, metalworking fluids, paints, lubricants, and electroless plating, to name a few. A key property to assess the quality (and thus value) of pure alkanolamines such as triethanolamine is color. In general, the less color, the higher its value. Thus, alkanolamine producers commonly have two objectives in providing pure alkanolamines: inhibiting color formation, and reducing color in discolored alkanolamines. Both of these objectives are referred to herein as "reducing color."

Fractional distillation of crude alkanolamines such as triethanolamine can readily produce a pure product that is initially colorless or near colorless. Such initially colorless product, however, can gradually develop color during storage, even upon storage in sealed containers in the dark. This color development can include initial pinking, followed by yellowing, cumulative yellowing, and further darkening to the extent of eventual formation of a brown color. Discoloration is even more rapid if the alkanolamine is exposed to light. The phenomenon of alkanolamines such as triethanolamine and other ethanolamines turning color is described, for example, in "SRI International, Process Economics Program Report no. 193" of January 1991, pp. 6-9 and 6-10.

Various methods to reduce color in triethanolamine have generally not been entirely satisfactory for various reasons. For example, discolored triethanolamine can be treated with additives such as potassium or sodium borohydride, ethylenediamine or its di-, tri- and tetra- homologs, alkali or alkaline earth metal borates, alkanolamine esters of boric acid, hydrazine, alkylene oxides, hydroxylamine, sodium hydroxide, sodium sulfites, or sulfurous acid. Hydrogen has been used to reduce the color of triethanolamine in the presence of heterogeneous hydrogenation catalysts at temperatures above 90° C.; phosphorous acid, hypophosphorous acid, phosphines, polymeric solid acid catalysts, activated clay, porcelain, silica gel or alumina gel has been added to triethanolamine before or during vacuum distillation of triethanolamine; and passing triethanolamine through a fixed bed of activated carbon has been used to improve its color. A number of these methods suffer from the drawback that they do not sufficiently remove color from discolored triethanolamine to the extent desired to give a colorless or near colorless product. Other methods can reduce color but cannot maintain a color-free product after color removal for a desired period of time. Moreover, certain methods to reduce color in triethanolamine have recently raised environmental and health concerns.

Other prior art techniques for reducing color in alkanolamines such as triethanolamine require two-stage vacuum distillation as described in US2004158102); use of a rectifying device as described in CN201524433U; use of a two-serial mixing and displacement apparatus as described in RU2430085C1; using a device for continuous manufacture and separation of triethanolamine (US2004127748A1), use of equipment made from substantially nickel-free alloy steel as described in U.S. Pat. No. 4,567,303; use of dividing wall columns as described in US20140061020A1 and CA2540246A1; use of a device comprising a distillation column and a downstream column as described in U.S. Pat. No. 8,466,323; as well as use of electromagnetic radiation, third column distillation, and short path and thin film evaporators. Disadvantages associated with these techniques include high investment cost for special equipment, cost for disposal of spent reagent after its use, as well as handling of hazardous materials.

There accordingly remains a need in the art for methods reducing color in alkanolamines such as triethanolamine, for maintaining reduced color in alkanolamines, as well as such reduced-color compositions.

SUMMARY

In an embodiment, a method of reducing color in alkanolamines comprises contacting the alkanolamine with a color-reducing amount of a borane complex effective to provide an alkanolamine composition having a Platinum-Cobalt Color Value, Test Method ASTM D1209, of less than 50, preferably less than 30, more preferably 0 to 20.

Also disclosed herein is a color-reduced triethanolamine composition comprising triethanolamine and an effective color-reducing amount of a borane complex, wherein the composition has a Platinum-Cobalt Color Value, Test Method ASTM D1209, of less than 50, preferably less than 30, more preferably 0 to less than or equal to 20.

DETAILED DESCRIPTION

As described above, unacceptable levels of color and color bodies can be found in finished, purified alkanolamines. Additionally, color bodies can form as contaminants in finished, pure alkanolamines over a period of time, for example during storage. The inventors hereof have discovered methods of reducing color in alkanolamines, or maintaining reduced color in alkanolamines. In a key feature of the methods, the alkanolamines are contacted with a borane complex to provide color-reduced alkanolamine compositions. Advantageously, after contacting, these alkanolamine compositions are colorless or near colorless to the human eye. In general, the compositions have a Platinum-Cobalt Color Value of less than 50, less than 30, more preferably 0 to 20, as determined according to Test Method ASTM D1209. In an especially advantageous feature, the low color can be maintained over months or years. Thus, in compositions treated to reduce color, or already having reduced color, the method can be used to maintain the low color over time. In another advantageous feature, the method is fast, and does not required expensive or time-consuming equipment. The reduced-color compositions can be directly packaged or transported.

The method is effective with a wide variety of alkanolamines, which includes linear, branched or cyclic compounds having at least one primary, secondary, or tertiary amino group and at least one alkanol group. Such alkanolamines include a mono($C_{1-10}$ alkanol)amine, a di($C_{1-10}$ alkanol)amine, a tri($C_{1-10}$ alkanol)amine, an N-($C_{1-10}$ alkyl) mono($C_{2-4}$ alkanol)amine, an N-($C_{1-10}$ alkyl) di($C_{2-4}$ alkanol)amine, an N,N-di($C_{1-10}$ alkyl) ($C_{2-4}$ alkanol)amine, an N-($C_{1-10}$ alkanol)pyrrolidine, alkanol)imidazolidine, an N-($C_{1-10}$ alkanol)piperidine, or an N-($C_{1-10}$ alkanol)piperazine. In some embodiments the alkanolamine is a mono($C_{1-4}$ alkanol)amine, a di($C_{1-4}$ alkanol)amine, a tri($C_{1-4}$ alkanol) amine, an N-($C_{1-4}$ alkyl) mono($C_{2-4}$ alkanol)amine, an N-($C_{1-4}$ alkyl) di($C_{2-4}$ alkanol)amine, an N,N-di($C_{1-4}$ alkyl) ($C_{2-4}$ alkanol)amine, an N-($C_{1-4}$ alkanol)pyrrolidine, N-($C_{1-4}$ alkanol)imidazolidine, an N-($C_{1-4}$ alkanol)piperidine, or an N-($C_{1-4}$ alkanol)piperazine Specific alkanolamines are monoethanolamine (MEA), diethanolamine (DEA), triethanolamine (TEA), methyl diethanolamine, isopropanolamine, diisopropanolamine, and (2-hydroxyethyl) piperazine. A combination comprising at least one of the foregoing alkanolamines can be used.

In some embodiments, the alkanolamine is triethanolamine. Methods for the manufacture of triethanolamine are known. For example, triethanolamine compositions can be made by a process that comprises distilling triethanolamine from a mixture that includes at least diethanolamine and triethanolamine in the presence of phosphorous acid ($H_3PO_3$). A method of preparation and distillation of triethanolamine is described in, for example, U.S. Pat. No. 6,323,371.

In an embodiment, the borane complex is of the formula

wherein L is ammonia ($NH_3$), hydrazine ($N_2H_4$), an organic amine, a thioether, an organic phosphine, or a heterocycle as further described below; each R is independently the same or different, and is a $C_{1-12}$ alkyl group, a $C_{3-8}$ cycloalkyl group, a $C_{3-7}$ heterocycloalkyl group, a $C_{6-10}$ aromatic group, or a $C_{3-15}$ heteroaromatic group, optionally wherein two R form a ring with the boron atom; and a is 0 to 2. Preferably the ring is a 4- to 6-membered ring optionally containing one or two nitrogen or oxygen ring members. Preferably each R is independently a $C_{1-6}$ alkyl group, a $C_{3-6}$ cycloalkyl group, or a $C_6$ aromatic group, and a is 0 to 2.

When L is ammonia ($NH_3$), the borane complex is of the formula $$H_3N \cdot BR_aH_{3-a}$$

wherein R is as defined above, and a is 0 to 2. In some embodiments L is ammonia and a is zero, such that the borane complex is of the formula $H_3N \cdot BH_3$, i.e., $NBH_6$. In some embodiments a is 1 or 2, and R is as defined above, or preferably each R is independently a $C_{1-6}$ alkyl group, a $C_{3-6}$ cycloalkyl group, or a $C_6$ aromatic group, optionally wherein two R form a ring with the boron atom; and more preferably each R is the same, for example the same $C_{1-3}$ alkyl group.

When the organic amine is selected as L, exemplary organic amines are a $C_{1-24}$ amine, preferably a $C_{1-24}$ amine of the formula:

wherein each $R^1$ is independently the same or different, and is hydrogen, provided that not all $R^1$ are hydrogen; or a $C_{1-8}$ hydrocarbyl group, optionally wherein any two $R^1$ form a ring with the nitrogen atom. In some embodiments each $R^1$ is independently hydrogen, a $C_{1-8}$ alkyl group, a $C_{3-8}$ cycloalkyl group, a $C_{3-7}$ heterocycloalkyl group, a $C_{6-18}$ aromatic group, or a $C_{3-15}$ heteroaromatic group, or any two $R^1$ together form a $C_{2-6}$ ring with the nitrogen atom that can optionally have 1 or 2 heteroatoms as ring members, and provided that not all $R^1$ are hydrogen. Preferably in some embodiments each $R^1$ is independently hydrogen or a $C_{1-6}$ alkyl group, most preferably hydrogen or a $C_{1-2}$ alkyl group, again provided that not all $R^1$ are hydrogen. Preferably in other embodiments, two $R^1$ are joined to form a 5- or 6-membered ring with the nitrogen, optionally further containing a nitrogen or oxygen atom as a ring member.

When the thioether is selected as L, examples of thioethers include a $C_{2-20}$ thioether, preferably a $C_{2-20}$ thioether of the formula:

wherein each $R^2$ is independently the same or different, and is a $C_{1-10}$ hydrocarbyl group. In some embodiments, each $R^2$ is independently a $C_{1-8}$ alkyl group, a $C_{3-8}$ cycloalkyl group, a $C_{3-7}$ heterocycloalkyl group, a $C_{6-10}$ aromatic group, or a $C_{3-15}$ heteroaromatic group. Preferably each $R^2$ is independently a $C_{1-6}$ alkyl group, most preferably a $C_{1-2}$ alkyl group.

Where the organic phosphine is selected as L, suitable organic phosphines include an organic phosphine substituted with three $C_{1-12}$ hydrocarbyl groups, preferably an organic phosphine of the formula:

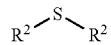

wherein each $R^3$ is independently the same or different, and is a $C_{1-12}$ hydrocarbyl group. In some embodiments each $R^3$ is independently a $C_{1-8}$ alkyl group, a $C_{3-8}$ cycloalkyl group, or a $C_{6-10}$ aromatic group. Preferably each $R^3$ is independently a $C_{1-6}$ alkyl group or $C_6$ aromatic group, most preferably a $C_{1-4}$ alkyl group or $C_6$ aromatic group.

When the heterocycle is selected as L, examples of heterocycles are a $C_{3-18}$ heterocycle. In some embodiments, the heterocycle is a $C_{3-18}$ aliphatic heterocycle, or a $C_{3-18}$ aromatic heterocycle. Examples of $C_{3-18}$ aliphatic heterocycles are a $C_{3-18}$ aliphatic heterocycle with 3 to 12 ring members wherein 1 to 10, or 1 to 8, or 1 to 6, or 1 to 4 ring members are each independently the same or different, and are a nitrogen, oxygen, phosphorus, silicon, or sulfur. In some embodiments the heterocycle is a $C_{3-12}$ aliphatic heterocycle with 3 to 8 ring members wherein 1 to 6, or 1 to 5, or 1 to 4, or 1 to 3 ring members are each independently the same or different, and are a nitrogen, oxygen, or sulfur. Preferably the heterocycle is a $C_{3-12}$ aliphatic heterocycle with 5 to 7 ring members wherein 1 or 2 ring members are each independently the same or different, and are a nitrogen, oxygen, or sulfur. In some embodiments the heterocycle is an aliphatic heterocycle of the formulas

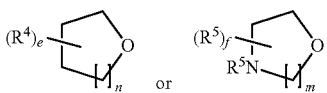

wherein each $R^4$ is independently the same or different, and is a $C_{1-6}$ alkyl group, a $C_{1-6}$ alkoxy group, a halogen, nitrile, or nitro group, $R^5$ is hydrogen or a $C_{1-6}$ alkyl group; e is 0 to 4, preferably 0; f is 0 to 3, preferably 0; n is 1 to 2, and m is 1 to 2, preferably 2.

Most preferably, the aliphatic heterocycle is of the formula

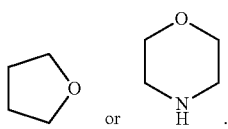 [SMILES: C1CCOC1 ; C1COCCN1]

Aliphatic heterocycles of these formulas are commonly known as tetrahydrofuran or morpholine.

Exemplary $C_{3-18}$ aromatic heterocycles include a $C_{3-18}$ aromatic heterocycle with 1 to 3 rings and 5 to 14 ring members wherein 1 to 10, or 1 to 6, or 1 to 4 ring members are each nitrogen, oxygen, or sulfur; preferably a $C_{3-18}$ aromatic heterocycle with 1 or 2 rings and 5 to 10 ring members wherein 1, 2, or 3 ring members are each independently the same or different, and are a nitrogen, oxygen, or sulfur, more preferably a $C_{3-18}$ aromatic heterocycle with 1 ring and 5 or 6 ring members wherein 1, 2, 3 ring members are each independently the same or different, and are a nitrogen, oxygen, or sulfur, most preferably an aromatic heterocycle of the formula

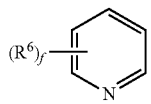

wherein each $R^6$ is independently the same or different, and is a $C_{1-12}$ hydrocarbyl group, preferably a $C_{1-8}$ alkyl group, a $C_{3-8}$ cycloalkyl group, or a $C_{6-10}$ aromatic group, more preferably a $C_{1-6}$ alkyl group, and f is 0 to 5.

Most preferably, the $C_{3-18}$ aromatic heterocycles include pyridine, i.e. f is 0.

In an embodiment, the borane complex is of the formula

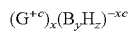

wherein G is an ammonium ion, a quaternary ammonium ion, a tertiary sulfonium ion, or a quaternary organic phosphonium ion, c is 1 to 3, x is 1 to 2, y is 2 to 20, and z is 4 to 14.

In other embodiments, the borane complex is of the formula

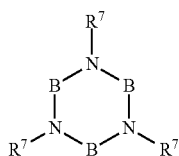

wherein each $R^7$ is independently the same or different and is a $C_{1-8}$ alkyl or a $C_{1-8}$ alkoxy.

In some preferred embodiments, the borane complex is of the formula $(R^1)_3N \cdot BRH_2$, wherein each $R^1$ is as defined above, and is specifically a hydrogen, a $C_{1-12}$ alkyl group, a $C_{3-8}$ cycloalkyl group, or a $C_{6-10}$ aromatic group, or two $R^1$ are joined to form a 5- or 6-membered ring optionally having a nitrogen or oxygen in the ring; and R is as defined above, and is specifically a $C_{1-12}$ alkyl group or a $C_{3-8}$ cycloalkyl group.

In other preferred embodiments, the borane complex is of the formula $(R^1)_3N \cdot B R_2H$, wherein each $R^1$ is as defined above, preferably wherein each $R^1$ is independently the same or different, and is hydrogen, a $C_{1-12}$ alkyl group, a $C_{3-8}$ cycloalkyl group, or a $C_{6-10}$ aromatic group provided that provided that not all $R^1$ are hydrogen or two $R^1$ are joined to form a 5- or 6-membered ring optionally having a nitrogen or oxygen in the ring; and each $R^8$ is independently the same or different, and is as described above, preferably a $C_{1-12}$ alkyl group or a $C_{3-8}$ cycloalkyl group.

Specific borane complexes include a borane-ammonia of the formula $H_3N \cdot BH_3$, i.e. $NBH_6$, borane-dimethylamine, borane-trimethyl amine, borane-triethyl amine, borane-tetrahydrofuran, borane-morpholine, borane-pyridine, or a combination comprising any one or more of the foregoing.

Many of the above-described complexes are commercially available. Also, methods for the manufacture of the above-described complexes are known. For example, borane ammonia can be prepared from an alkali metal borohydride and ammonium salts, e.g., sodium borohydride and ammonium chloride, or by reacting diethyl ether-borane with ammonia. A process for the synthesis of ammonia borane is described in, for example, U.S. Pat. No. 7897129. Alkylaminoboranes can be obtained by reaction of an alkali metal borohydride with an alkylammonium salts. Other boranes are described, for example, in Staubitz, A. et al., Chemical Reviews, Vol. 110, No. 7, pp. 4023-78 (2010), and references cited therein; and in Brown, H. C. et al., "Organic Syntheses via Boranes", John Wiley & Sons (1975) and references cited therein; and in Brunel J. M. et al., Coordination Chemistry Reviews, Vols. 178-180, Part 1 pp. 665-698 (1998) and references cited therein.

The alkanolamine compositions can have any level of color before treatment with a borane complex, including low, very low, or no color before treatment with the borane complex. As described in more detail below, treatment of alkanolamine compositions having low, very, low, or no color can be to prevent color formation over time. For convenience, any alkanolamine composition treated with a borane complex as described herein can be referred to as a "color-reduced alkanolamine composition."

Contacting the alkanolamines with the borane complex can be at a temperature from 20° C. to 250° C., preferably 20° C. to 150° C., more preferably 20° C. to 90° C., more preferably still 20° C. to 45° C., or 20° C. to 30° C. Lower temperatures (e.g., 20° C. to 30° C. are preferred to prevent side reactions that can cause color. Contacting can generally be for a selected period of time, for example, 10 minutes to 50 hours, preferably 30 minutes to 30 hours, more preferably 1 hour to 24 hours. Contacting can be by mixing of the alkanolamine and the borane complex, during or after the contacting. It is to be understood that the borane complex is generally not subsequently quenched or removed from the alkanolamine, such that the above contacting temperatures and times may simply be for an initial period before the alkanolamine is further processed, for example transported or packaged for storage or transportation.

For the purpose of contacting, the borane complex is used neat or in solution. When used in solution, the borane complex is dissolved in a solvent before contacting to form a solution. Examples of the solvent are water and alcohol to form an aqueous or alcoholic solution, preferably an aqueous solution, a $C_{1-3}$ alcoholic solution, more preferably a $C_{1-2}$ alcoholic solution. In these solutions, the concentration of the borane complex is 1 to 30 weight percent (wt %), based on total weight of the solution, preferably 1 to 20 wt %, more preferably 1 to 20 wt %, even more preferably 1 to 10 wt %.

When contacting the alkanolamine with the borane complex, the borane complex is generally present in an amount effective to reduce color. For example, the concentration of the borane complex can be from 1 to 5,000 ppm (where ppm denotes parts per million by weight based on the weight of the alkanolamine), preferably 5 to 2,000 ppm, more preferably 5 to 1,000 ppm, more preferably still 5 to 500 ppm.

Contacting the alkanolamines with the borane complex reduces any initial color, e.g., color bodies and color contaminants, present in the alkanolamines before such contact, and provides the color-reduced alkanolamine compositions herein. The inventors hereof have advantageously found that such initial color is reduced during or after contacting to the extent that the resultant alkanolamine compositions are colorless or near colorless. Without wishing to be bound by any specific theory, borane is believed to be liberated during contacting and acts as a reducing agent, of any color bodies or contaminants that cause color bodies present in the alkanolamines.

The color-reduced alkanolamine compositions produced by the methods described herein, for example reduced-color triethanolamine compositions, can have significantly reduced or low color. For example, the Hazen color, specifically the Platinum-Cobalt Color Value as determined according to Test Method ASTM D1209 ("Pt—Co color value") can be less than 50, and preferably less than 30. It has surprisingly been found that the Pt—Co color value can be 0 to 20.

Further advantageously, the color-reduced alkanolamine compositions produced by these methods, specifically reduced-color triethanolamine compositions, can maintain these very low color values over extended periods. The borane complexes can thus prevent color increases over time. For example, the color-reduced alkanolamine compositions produced by the methods described herein, specifically color-reduced triethanolamine compositions, when stored at room temperature (e.g., 20° C. to 25° C.) for a period of six months to one year, or one to two years, or one to three years, or one year to six years, following the contacting, can have a Pt—Co color value of less than 50, preferably less than 30, more preferably 0 to 20. In some embodiments, the color-reduced alkanolamine compositions can have a Pt—Co color value of less than 50, preferably less than 30, more preferably 0 to 20, after storage at room temperature (e.g., 20° C. to 25° C.) for a period of six months to eight years, or one to eight years, or two to eight years, or three to seven years, or four to six years, following the contacting when protected from light. "Storage" as used herein includes periods where the compositions are not in active use, for example where the compositions are transported. "Protected from light" can mean that the compositions are stored under conditions where visible light is excluded for at least 90% of the time during storage.

In other embodiments, the color-reduced alkanolamine compositions produced by the methods described herein, specifically color-reduced triethanolamine compositions, can have a Pt-Co color value that does not increase by more than 40%, preferably more than 30%, more preferably more than 20% when stored at room temperature (e.g., 20° C. to 25° C.) for a period of six months to eight years, or one to eight years, or two to eight years, or three to seven years, or four to six years, following the contacting. In some embodiments, the color-reduced alkanolamine compositions produced by the methods described herein, specifically color-reduced triethanolamine compositions, can have a Pt—Co color value that does not increase by more than 40%, preferably more than 30%, more preferably more than 20% when stored at room temperature (e.g., 20° C. to 25° C.) for a period for a period of six months to eight years, or one to eight years, or two to eight years, or three to seven years, or four to six years, when protected from light.

The alkanolamine compositions produced by these methods are also color-stable at elevated temperatures. Thus, the color-reduced alkanolamine compositions produced by the methods described herein, specifically color-reduced triethanolamine compositions, when stored at 30° C. to 50° C., or 40 to 50° C., or 45° C., for a period of one month to three years, or one month to two years, or three months to one year, or four to eight months following the contacting, can have a Pt—Co color value of less than 50, preferably less than 30, more preferably 0 to 20. In some embodiments, the color-reduced alkanolamine compositions can have a Pt—Co color value of less than 50, preferably less than 30, more preferably 0 to 20, after storage at 30° C. to 50° C., or 40° C. to 50° C., or 45° C., for a period of one month to three years, or one month to two years, or three months to one year, or 4 to 8 months following the contacting when protected from light. In some embodiments, the color-reduced alkanolamine compositions produced by the methods described herein, specifically color-reduced triethanolamine compositions, can have a Pt—Co color value that does not increase by more than 40%, preferably more than 30%, more preferably more than 20% when stored at 30° C. to 50° C., or 40° C. to 50° C., or 45° C., for a period of one month to three years, or one month to two years, or three months to one year, or 4 to 8 months when protected from light.

As mentioned above, an advantage of this method is that the alkanolamine compositions do not require subsequent purification or processing after being contacted with the borane complex. Residual boron levels in the color-reduced compositions can accordingly be 0.1 to 5000 ppm of residual boron, preferably 5 to 2,000 ppm, more preferably 5 to 500 ppm, or 1 to 100 ppm. The term "residual boron" encompasses boron in any form, for example in elemental form, as the complex, or in combination with one or more boron complex reaction products. The term "residual boron" further includes any boron present in the alkanolamine compositions before or after addition of the boron complex, and may thus be higher than the amount of boron added as the complex.

Accordingly, color-reduced alkanolamine compositions comprising an alkanolamine and 0.1 to 5000 ppm of residual boron, preferably 5 to 2,000 ppm of residual boron, more preferably 5 to 500 ppm of residual boron, can have a Pt—Co color value of less than 50, and preferably less than 30. In a preferred embodiment, the Pt—Co color value can be 0 to 20. In some embodiments, color-reduced triethanolamine compositions comprising triethanolamine and 0.1 to 5,000 ppm of residual boron, preferably 5 to 2,000 ppm of residual boron, more preferably 5 to 500 ppm of residual boron, can have a Pt—Co color value of less than 50, and preferably less than 30. In a preferred embodiment, the Pt—Co color value of the color-reduced triethanolamine composition comprising residual boron can be 0 to 20.

In still other embodiments, unreacted (residual) boron complex can remain in the color-reduced compositions. Accordingly, color-reduced alkanolamine compositions comprising an alkanolamine and 0.1 to 4,900 ppm of residual boron complex, or 0.1 to 3,000 ppm of residual boron complex, or 0.1 to 1,000 ppm of residual boron complex, or 0.1 to 500 ppm of residual boron complex can have a Pt—Co color value of less than 50, and preferably less than 30. In a preferred embodiment, the Pt—Co color value can be 0 to 20. In some embodiments, color-reduced triethanolamine compositions comprising triethanolamine and 0.1 to 4,990 ppm of residual boron complex, or 0.1 to 3,000 ppm of residual boron complex, or 0.1 to 1,000 ppm of residual boron complex, or 0.1 to 500 ppm of residual boron complex, can have a Pt—Co color value of less than 50, and preferably less than 30. In a preferred embodiment, the Pt—Co color value of the color-reduced triethanolamine composition comprising residual boron complex can be 0 to 20.

The color-reduced alkanolamine compositions can maintain these very low color values over extended time. For example the color-reduced alkanolamine compositions comprising an alkanolamine and 0.1 to 5000 ppm of residual boron, or 5 to 2,000 ppm of residual boron, or 5 to 500 ppm of residual boron, after storage at room temperature (e.g., 20° C. to 25° C.) for a period of six months to eight years, or one to eight years, or two to eight years, or three to seven years, or four to six years, following the contacting, can have a Pt—Co color value of less than 50, preferably less than 30, more preferably 0 to 20. The color-reduced alkanolamine compositions can have a Pt—Co color value of less than 50, preferably less than 30, more preferably 0 to 20 after storage at room temperature (e.g., 20° C. to 25° C.) for a period of six months to eight years, or one to eight years, or two to eight years, or three to seven years, or four to six years, when the compositions are protected from light.

In some embodiments, color-reduced triethanolamine compositions comprising triethanolamine and 0.1 to 5000 ppm of residual boron, preferably 5 to 2,000 ppm of residual boron, more preferably 5 to 500 ppm of residual boron, after storage at room temperature (e.g., 20° C. to 25° C.) for a period of six months to eight years, or one to eight years, or two to eight years, or three to seven years, or four to six years, following the contacting, can have a Pt—Co color value less than 50, and preferably less than 30. In a preferred embodiment, the Pt—Co color value of the color-reduced triethanolamine composition comprising residual boron can be 0 to 20 for a period of six months to eight years, or one to eight years, or two to eight years, or three to seven years, or four to six years, following contacting. The color-reduced triethanolamine compositions can have Pt—Co color value of less than 50, preferably less than 30, more preferably 0 to 20 after storage at room temperature (e.g., 20° C. to 25° C.) for a period of six months to for a period of six months to eight years, or one to eight years, or two to eight years, or three to seven years, or four to six years after contacting when the compositions are protected from light.

In some embodiments where the compositions contain residual boron complex, the color-reduced alkanolamine compositions can maintain these very low color values over extended time. For example the color-reduced alkanolamine compositions comprising an alkanolamine and 0.1 to 4,500 ppm of residual boron complex, or 1 to 2,000 ppm of residual boron complex, or 5 to 1,000 ppm of residual boron complex, after storage at room temperature (e.g., 20° C. to 25° C.) for a period of six months to eight years, or one to eight years, or two to eight years, or three to seven years, or four to six years, following the contacting, can have a Pt—Co color value of less than 50, preferably less than 30, more preferably 0 to 20. The color-reduced alkanolamine compositions can have a Pt—Co color value of less than 50, preferably less than 30, more preferably 0 to 20 after storage at room temperature (e.g., 20° C. to 25° C.) for a period of six months to eight years, or one to eight years, or two to eight years, or three to seven years, or four to six years, when the compositions are protected from light.

In some embodiments, color-reduced triethanolamine compositions comprising triethanolamine and 0.1 to 4,990 ppm of residual boron complex, or 0.1 to 3,000 ppm of residual boron complex, or 0.1 to 1,000 ppm of residual boron complex, or 0.1 to 500 ppm of residual boron complex, after storage at room temperature (e.g., 20° C. to 25° C.) for a period of six months to eight years, or one to eight years, or two to eight years, or three to seven years, or four to six years, following the contacting, can have a Pt—Co color value less than 50, and preferably less than 30. In a preferred embodiment, the Pt—Co color value of the color-reduced triethanolamine composition comprising residual boron complex can be 0 to 20 for a period of six months to eight years, or one to eight years, or two to eight years, or three to seven years, or four to six years, following contacting. The color-reduced triethanolamine compositions can have Pt—Co color value of less than 50, preferably less than 30, more preferably 0 to 20 after storage at room temperature (e.g., 20° C. to 25° C.) when the compositions are protected from light.

The reduced-color alkanolamine compositions can include water. For example, water can be present in the compositions in an amount of less than 10 weight percent (wt. %), preferably less than 5 wt. %, more preferably less than 3 wt. %, even more preferably less than 1 wt. %, even more preferably still less than 0.5 wt. %, based on the total weight of the reduced-color alkanolamine composition.

The alkanolamine compositions can be used for example as emulsifiers, surfactants, solvents, co-solvents, pH adjusting agents, or buffering agents, as well as in any other known uses, in a wide variety of applications. Such applications include household goods, cement production, cosmetics, medicine, printing, chemical manufacturing (e.g., as a solvent, catalyst, or reactant, and electroless plating. Some products that can include the alkanolamines include liquid laundry detergents, dishwashing liquids, general cleaners, hand cleaners, polishes, metalworking fluids, paints, shaving cream, and printing inks.

The following Examples are provided for illustrative purposes only and are not to be construed as limiting in any manner.

EXAMPLES

Color determination was carried out on a Lico® 690 Colorimeter from Koehler Instrument Company in accordance with the Pt—Co test method as described in ASTM D1209 (2011). Results are reported as Pt—Co Color Values.

Example 1

Color Stability of a Color-Reduced Triethanolamine Composition

Triethanolamine (1000 g, Sigma Aldrich, 99% purity) having a Pt—Co Color Value of 23 is mixed with a borane-ammonia complex (100 mg, obtained from Sigma Aldrich, 95% purity). The mixture is vigorously shaken to allow the borane-ammonia complex to distribute homogenously in the triethanolamine. Over a period of 6 hours the mixture clears. A sample is taken for color analysis, and found to have a Pt—Co Color Value that was calculated to be less than 15 after 2 years at room temperature (20-25° C.).

Example 2

A sample of triethanolamine (TEA) with a borane-ammonia complex was stored in an oven at 45° C. for six months. The sample was removed, cooled, and found to have a Pt—Co Color Value of 20. According to Van't Hoff's law, chemical reaction rates double to quadruple for every 10 degrees Celsius increase in temperature. It is therefore calculated that if TEA with borane complex was stored at room temperature (25° C.), its color index would be less than 20 for as long as 6 years (if reaction rate quadrupled every 10° C. increase).

The methods and compositions are further illustrated by the following embodiments.

Embodiment 1: A method of reducing color in an alkanolamine, the method comprising: contacting the alkanolamine with a color-reducing amount of a borane complex effective to provide an alkanolamine composition having a Platinum-Cobalt Color Value, Test Method ASTM D1209, of less than 50, preferably less than 30, more preferably 0 to 20.

Embodiment 2: The method of embodiment 1, wherein the alkanolamine is a mono($C_{1-10}$ alkanol)amine, a di($C_{1-10}$ alkanol)amine, a tri($C_{1-10}$ alkanol)amine, an N-($C_{1-10}$ alkyl) di($C_{2-4}$ alkanol)amine, an N,N-di($C_{1-10}$ alkyl) ($C_{2-4}$ alkanol) amine, an N-($C_{1-10}$ alkanol)pyrrolidine, N-($C_{1-10}$ alkanol) imidazolidine, an N-($C_{1-10}$ alkanol)piperidine, an N-($C_{1-10}$ alkanol)piperazine or a combination comprising at least one of the foregoing; preferably monoethanolamine, diethanolamine, methyldiethanolamine, isopropanolamine, diisopropanolamine, (2-hydroxyethyl)piperazine, or a combination comprising at least one of the foregoing.

Embodiment 3: The method of embodiment 1, wherein the alkanolamine is a tri($C_{1-10}$ alkanol)amine, preferably triethanolamine.

Embodiment 4: The method of any one or more of embodiments 1 to 3, wherein: the borane complex is of the formula L·BR$_a$H$_{3-a}$ wherein L is ammonia, hydrazine, an organic amine, a thioether, an organic phosphine, or a heterocycle, each R is independently a $C_{1-12}$ alkyl group, a $C_{3-8}$ cycloalkyl group, a $C_{3-7}$ heterocycloalkyl group, a $C_{6-10}$ aromatic group, or a $C_{3-15}$ heteroaromatic group, optionally wherein any two R form a ring with the boron atom; and a is 0 to 2; the borane complex is of the formula $(G^{+c})_x(B_yH_z)^{-xc}$, wherein G is an ammonium ion, a quaternary ammonium ion, a tertiary sulfonium ion, or a quaternary organic phosphonium ion, c is 1 to 3, x is 1 to 2, y is 2 to 20, and z is 4 to 14; or the borane complex is of the formula

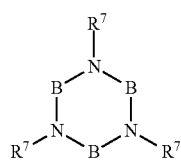

wherein each $R^7$ is independently a $C_{1-8}$ alkyl or a $C_{1-8}$ alkoxy.

Embodiment 5: The method of any one or more of embodiments 1 to 4, wherein: the borane complex is of the formula L·BH$_3$, wherein L is ammonia or a $C_{1-24}$ organic amine, an organic phosphine substituted with three $C_{1-12}$ hydrocarbyl groups, a $C_{3-18}$ heterocycle, or a $C_{2-20}$ thioether; or the borane complex is of the formula H$_3$N·BR$_a$H$_{3-a}$, wherein a is 1 or 2, and each R is independently the same or different, and is a $C_{1-12}$ alkyl group, a $C_{3-8}$ cycloalkyl group, a $C_{3-7}$ heterocycloalkyl group, a $C_{6-10}$ aromatic group, or a $C_{3-15}$ heteroaromatic group, optionally wherein two R form a ring with the boron atom, preferably wherein each R is independently a $C_{1-6}$ alkyl group, a $C_{3-6}$ cycloalkyl group, or a $C_6$ aromatic group.

Embodiment 6: The method of embodiment 5, wherein L is ammonia or a $C_{1-24}$ amine of the formula $(R^1)_3N$ wherein each $R^1$ is independently hydrogen or a $C_{1-8}$ hydrocarbyl group, optionally wherein any two $R^1$ form a ring with the nitrogen atom, and provided that not all $R^1$ are hydrogen; or hydrogen, a $C_{1-8}$ alkyl group, a $C_{3-8}$ cycloalkyl group, a $C_{3-7}$ heterocycloalkyl group, a $C_{6-18}$ aromatic group, or a $C_{3-15}$ heteroaromatic group, or any two $R^1$ together form a $C_{2-6}$ ring with the nitrogen atom that can optionally have 1 or 2 heteroatoms as ring members, and provided that not all $R^1$ are hydrogen, more preferably hydrogen or a $C_{1-6}$ alkyl group, or two $R^1$ are joined to form a 5- or 6-membered ring with the nitrogen, optionally further containing a nitrogen or oxygen atom as a ring member, and provided that not all $R^1$ are hydrogen; most preferably hydrogen or a $C_{1-2}$ alkyl group, or two $R^1$ are joined to form a morpholine, and provided that not all $R^1$ are hydrogen.

Embodiment 7: The method of embodiment 5, wherein L is an organic phosphine of the formula $(R^3)_3P$, wherein each $R^3$ is independently a $C_{1-12}$ hydrocarbyl group, preferably a $C_{1-8}$ alkyl group, a $C_{3-8}$ cycloalkyl group, or a $C_{6-10}$ aromatic group, more preferably a $C_{1-6}$ alkyl group or $C_6$ aromatic group, most preferably a $C_{1-4}$ alkyl group or $C_6$ aromatic group.

Embodiment 8: The method of embodiment 5, wherein L is a $C_{2-20}$ thioether of the formula $(R^2)_2S$ wherein each $R^2$ is independently a $C_{1-10}$ hydrocarbyl group, preferably a $C_{1-8}$ alkyl group, a $C_{3-8}$ cycloalkyl group, a $C_{3-7}$ heterocycloalkyl group, a $C_{6-10}$ aromatic group, or a $C_{3-15}$ heteroaromatic group, more preferably a $C_{1-6}$ alkyl group, most preferably a $C_{1-2}$ alkyl group.

Embodiment 9: The method of embodiment 5, wherein L is a $C_{3-18}$ aliphatic heterocycle with 3 to 12 ring members wherein 1, 2, or 3 ring members are each independently nitrogen, oxygen, phosphorus, silicon, or sulfur; preferably a $C_{3-12}$ aliphatic heterocycle with 3 to 8 ring members wherein 1, 2, or 3 ring members are each independently nitrogen, oxygen, or sulfur, more preferably a $C_{3-12}$ aliphatic heterocycle with 5 to 7 ring members wherein 1 or 2 ring members are each independently nitrogen, oxygen, or sulfur, still more preferably an aliphatic heterocycle of the formulas

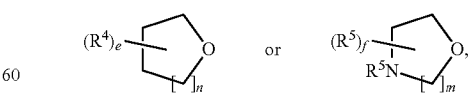

wherein each $R^4$ is independently a $C_{1-6}$ alkyl group, a $C_{1-6}$ alkoxy group, a halogen, nitrile, or nitro group, $R^5$ is hydrogen or a $C_{1-6}$ alkyl group, e is 0 to 4, preferably 0, f is 0 to 3, preferably 0, n is 1 to 2, and m is 1 to 2, preferably 2; most preferably an aliphatic heterocycle of the formulas

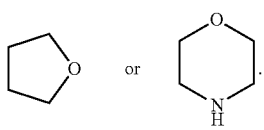 [SMILES: C1CCOC1 ; C1COCCN1]

Embodiment 10: The method of embodiment 5, wherein L is a $C_{3-18}$ aromatic heterocycle with 1 to 3 rings and 5 to 14 ring members wherein 1, 2, or 3 ring members are each independently nitrogen, oxygen, or sulfur; preferably a $C_{3-18}$ aromatic heterocycle with 1 or 2 rings and 5 to 10 ring members wherein 1, 2, or 3 ring members are each independently nitrogen, oxygen, or sulfur, more preferably a $C_{3-18}$ aromatic heterocycle with 1 ring and 5 or 6 ring members wherein 1, 2, 3 ring members are each independently nitrogen, oxygen, or sulfur, most preferably an aromatic heterocycle of the formula

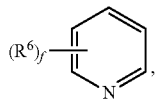

wherein each $R^6$ is independently a $C_{1-12}$ hydrocarbyl group, preferably a $C_{1-8}$ alkyl group, a $C_{3-8}$ cycloalkyl group, or a $C_{6-10}$ aromatic group, more preferably a $C_{1-6}$ alkyl group, and f is 0 to 5;

most preferably wherein L is pyridine.

Embodiment 11: The method of embodiment 5, wherein L is ammonia, dimethylamine, trimethylamine, triethylamine, tetrahydrofuran, morpholine, or pyridine.

Embodiment 12: The method of any one or more of embodiments 1 to 11, wherein contacting is with 1 to 5,000 ppm by weight of the borane complex, or 5 to 2,000 ppm, or 5 to 1,000 ppm, based on the weight of the alkanolamine.

Embodiment 13: The method of any one or more of embodiments 1 to 12, wherein the borane complex is dissolved in a solvent before contacting, preferably an aqueous or alcoholic solvent, preferably an aqueous or a $C_{1-2}$ alcoholic solvent.

Embodiment 14: The method of embodiment 13, wherein the concentration of the borane complex in the solvent is 1 to 30 wt %, based on total weight of the components, preferably 1 to 20 wt %, more preferably 1 to 20 wt %, even more preferably 1 to 10 wt %.

Embodiment 15: The method of any one or more of embodiments 1 to 14, further comprising mixing the alkanolamine and the borane complex during or after the contacting.

Embodiment 16: The method of any one or more of embodiments 1 to 15, wherein the contacting is at 20° C. to 250° C., preferably 20° C. to 40° C., more preferably 20° C. to 30° C.; and for 10 minutes to 50 hours.

Embodiment 17: The method of any one or more of embodiments 1 to 16, wherein the Platinum-Cobalt Color Value, Test Method ASTM D1209, does not increase by more than 40%, preferably more than 30%, or more preferably more than 20% for a period of six months to eight years, or one to eight years, or two to eight years, or three to seven years, or four to six years, after storage at room temperature.

Embodiment 18: The method of any one or more of embodiments 1 to 17, wherein the Platinum-Cobalt Color Value, Test Method ASTM D1209, does not increase by more than 40%, preferably more than 30%, more preferably more than 20% for a period of one month to three years, or one month to two years, or three months to one year, or 4 to 8 months after storage at 45° C.

Embodiment 19: A color-reduced alkanolamine composition, the composition comprising: triethanolamine and an effective color-reducing amount of a borane complex, wherein the composition has a Platinum-Cobalt Color Value, Test Method ASTM D1209, of less than 50, preferably less than 30, more preferably 0 to less than or equal to 20.

Embodiment 20: The composition of embodiment 19, wherein the alkanolamine is a mono($C_{1-10}$ alkanol)amine, a di($C_{1-10}$ alkanol)amine, a tri($C_{1-10}$ alkanol)amine, an N-($C_{1-10}$ alkyl) di($C_{2-4}$ alkanol)amine, an N,N-di($C_{1-10}$ alkyl) ($C_{2-4}$ alkanol)amine, or a combination comprising at least one of the foregoing; preferably monoethanolamine, diethanolamine, methyldiethanolamine, isopropanolamine, diisopropanolamine, (2-hydroxyethyl)piperazine, or a combination comprising at least one of the foregoing.

Embodiment 21: The composition of any one or more of embodiments 19 to 20, wherein the alkanolamine is a tri($C_{1-10}$ alkanol)amine, preferably triethanolamine.

Embodiment 22: The composition of any one or more of embodiments 19 to 21, wherein: the borane complex is of the formula $L \cdot BR_aH_{3-a}$, wherein L is ammonia, hydrazine, an organic amine, a thioether, an organic phosphine, or a heterocycle; each R is independently is a $C_{1-12}$ alkyl group, a $C_{3-8}$ cycloalkyl group, a $C_{3-7}$ heterocycloalkyl group, a $C_{6-10}$ aromatic group, or a $C_{3-15}$ heteroaromatic group, optionally wherein any two R form a ring with the boron atom; and a is 0 to 2; the borane complex is of the formula $(G^{+c})_x(B_yH_z)^{-xc}$, wherein G is an ammonium ion, a quaternary ammonium ion, a tertiary sulfonium ion, or a quaternary organic phosphonium ion, c is 1 to 3, x is 1 to 2, y is 2 to 20, and z is 4 to 14; or the borane complex is of the formula

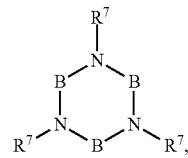

wherein each $R^7$ is independently a $C_{1-8}$ alkyl or a $C_{1-8}$ alkoxy.

Embodiment 23: The composition of any one or more of embodiments 19 to 22, wherein: the borane complex is of the formula $LBH_3$ wherein each L is independently ammonia or a $C_{1-24}$ organic amine, an organic phosphine substituted with three $C_{1-12}$ hydrocarbyl groups, a $C_{3-18}$ heterocycle, or a $C_{2-20}$ thioether; or ; or the borane complex is of the formula $H_3N \cdot BR_aH_{3-a}$, wherein a is 1 or 2, and each R is independently the same or different, and is a $C_{1-12}$ alkyl group, a $C_{3-8}$ cycloalkyl group, a $C_{3-7}$ heterocycloalkyl group, a $C_{6-10}$ aromatic group, or a $C_{3-15}$ heteroaromatic group, optionally wherein two R form a ring with the boron atom, preferably wherein each R is independently a $C_{1-6}$ alkyl group, a $C_{3-6}$ cycloalkyl group, or a $C_6$ aromatic group.

Embodiment 24: The composition of embodiment 23, wherein L is ammonia or a $C_{1-24}$ amine of the formula $(R^1)_3N$, wherein each $R^1$ is the independently hydrogen or a $C_{1-8}$ hydrocarbyl group, optionally wherein any two $R^1$ form a ring with the nitrogen atom, and provided that not all $R^1$ are hydrogen, or hydrogen, a $C_{1-8}$ alkyl group, a $C_{3-8}$ cycloalkyl group, a $C_{3-7}$ heterocycloalkyl group, a $C_{6-18}$ aromatic group, or a $C_{3-15}$ heteroaromatic group, or any two $R^1$ together form a $C_{2-6}$ ring with the nitrogen atom that can optionally have 1 or 2 heteroatoms as ring members, and provided that not all $R^1$ are hydrogen, more preferably hydrogen or a $C_{1-6}$ alkyl group, two $R^1$ are joined to form a 5- or 6-membered ring with the nitrogen, optionally further containing a nitrogen or oxygen atom as a ring member, and provided that not all $R^1$ are hydrogen most preferably hydrogen or a $C_{1-2}$ alkyl group, or two $R^1$ are joined to form a morpholine, and provided that not all $R^1$ are hydrogen.

Embodiment 25: The composition of embodiment 23, wherein L is an organic phosphine of the formula $(R^3)_3P$, wherein each $R^3$ is independently a $C_{1-12}$ hydrocarbyl group, preferably a $C_{1-8}$ alkyl group, a $C_{3-8}$ cycloalkyl group, or a $C_{6-10}$ aromatic group, more preferably a $C_{1-6}$ alkyl group or $C_6$ aromatic group, most preferably a $C_{1-4}$ alkyl group or $C_6$ aromatic group.

Embodiment 26: The composition of embodiment 23, wherein L is a $C_{2-20}$ thioether of the formula $(R^2)_3S$, wherein each $R^2$ is independently a $C_{1-10}$ hydrocarbyl group, preferably a $C_{1-8}$ alkyl group, a $C_{3-8}$ cycloalkyl group, a $C_{3-7}$ heterocycloalkyl group, a $C_{6-10}$ aromatic group, or a $C_{3-15}$ heteroaromatic group, more preferably a $C_{1-6}$ alkyl group, most preferably a $C_{1-2}$ alkyl group.

Embodiment 27: The composition of embodiment 23, wherein L is a $C_{3-18}$ aliphatic heterocycle with 3 to 12 ring members wherein 1, 2, or 3 ring members are each independently nitrogen, oxygen, phosphorus, silicon, or sulfur; preferably a $C_{3-12}$ aliphatic heterocycle with 3 to 8 ring members wherein 1, 2, or 3 ring members are each independently nitrogen, oxygen, or sulfur, more preferably a $C_{3-12}$ aliphatic heterocycle with 5 to 7 ring members wherein 1 or 2 ring members are each independently nitrogen, oxygen, or sulfur, still more preferably an aliphatic heterocycle of the formulas

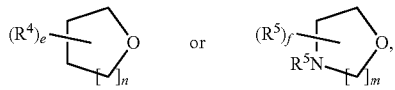

wherein each $R^5$ is independently a $C_{1-6}$ alkyl group, a $C_{1-6}$ alkoxy group, a halogen, nitrile, or nitro group, $R^6$ is hydrogen or a $C_{1-6}$ alkyl group, e is 0 to 4, preferably 0, f is 0 to 3, preferably n0 is 1 to 2, and m is 1 to 2, preferably 2; most preferably an aliphatic heterocycle of the formulas

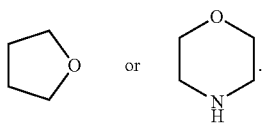 [SMILES: C1CCOC1 ; C1COCCN1]

Embodiment 28: The composition of embodiment 23, wherein L is a $C_{3-18}$ aromatic heterocycle with 1 to 3 rings and 5 to 14 ring members wherein 1, 2, or 3 ring members are each independently nitrogen, oxygen, or sulfur; preferably a $C_{3-18}$ aromatic heterocycle with 1 or 2 rings and 5 to 10 ring members wherein 1, 2, or 3 ring members are each independently nitrogen, oxygen, or sulfur, more preferably a $C_{3-18}$ aromatic heterocycle with 1 ring and 5 or 6 ring members wherein 1, 2, 3 ring members are each independently nitrogen, oxygen, or sulfur, most preferably an aromatic heterocycle of the formula

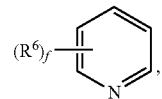

wherein each $R^6$ is independently a $C_{1-12}$ hydrocarbyl group, preferably a $C_{1-8}$ alkyl group, a $C_{3-8}$ cycloalkyl group, or a $C_{6-10}$ aromatic group, more preferably a $C_{1-6}$ alkyl group, and f is 0 to 5; most preferably wherein L is pyridine.

Embodiment 29: The composition of embodiment 23, wherein L is ammonia, dimethylamine, trimethylamine, triethylamine, tetrahydrofuran, morpholine, or pyridine.

Embodiment 30: The composition of any one or more of embodiments 19 to 29, comprising 1 to 5,000 ppm by weight of the boron complex, preferably 5 to 2,000 ppm, or more preferably 5 to 1,000 ppm, based on the parts by weight of the triethanolamine.

Embodiment 31: The composition of any one or more of embodiments 19 to 30, comprising less than 5 wt % of water, preferably less than 1 wt % of water, based on the total weight of the triethanolamine.

Embodiment 32: The composition of any one or more of embodiments 19 to 31, wherein the Platinum-Cobalt Color Value, Test Method ASTM D1209, does not increase by more than 40%, preferably more than 30%, more preferably more than 20% for a period of six months to eight years, or one to eight years, or two to eight years, or three to seven years, or four to six years, after storage at room temperature.

Embodiment 33: The composition of any one or more of embodiments 19 to 32, wherein the Platinum-Cobalt Color Value, Test Method ASTM D1209, does not increase by more than 40%, preferably more than 30%, more preferably more than 20% for a period of one month to three years, or one month to two years, or three months to one year, or 4 to 8 months, after storage at 45° C.

In general, the methods and compositions can alternatively comprise, consist of, or consist essentially of, any appropriate steps or components herein disclosed. The methods or compositions can additionally, or alternatively, be formulated so as to be devoid, or substantially free, of any steps, components, materials, ingredients, adjuvants or species used in the prior art compositions or that are otherwise not necessary to the achievement of the function and/or objectives described herein.

The singular forms "a," "an," and "the" include plural referents unless the context clearly dictates otherwise. "Or" means "and/or." The endpoints of all ranges directed to the same component or property are inclusive and independently combinable. Disclosure of a narrower range or more specific group in addition to a broader range is not a disclaimer of the broader range or larger group. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

As used herein, the term "hydrocarbyl" includes groups containing carbon, hydrogen, and optionally one or more heteroatoms (e.g., 1, 2, 3, or 4 atoms such as halogen, O, N, S, P, or Si). "Alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—$CH_2$—) or propylene (—$(CH_2)_3$—)). "Alkenyl" and "alkenylene" mean a monovalent or divalent, respectively, straight or branched chain hydrocarbon group having at least one carbon-carbon double bond (e.g., ethenyl (—HC=CH2) or propenylene (—HC($CH_3$)=$CH_2$—). "Alkynyl" means a straight or branched chain, monovalent hydrocarbon group having at least one carbon-carbon triple bond (e.g., ethynyl). "Alkoxy" means an alkyl group linked via an oxygen (i.e., alkyl-O—), for example methoxy, ethoxy, and sec-butyloxy. "Cycloalkyl" and "cycloalkylene" mean a monovalent and divalent cyclic hydrocarbon group, respectively, of the formula —$C_nH_{2n-x}$ and —$C_nH_{2n-2x}$— wherein x is the number of cyclization(s). "Aryl" means a monovalent, monocyclic or polycyclic, aromatic group (e.g., phenyl or naphthyl). "Arylene" means a divalent, monocyclic or polycyclic, aromatic group (e.g., phenylene or naphthylene). The prefix "halo" means a group or compound including one more halogen (F, Cl, Br, or I) substituents, which can be the same or different. The prefix "hetero" means a group or compound that includes at least one ring member that is a heteroatom (e.g., 1, 2, or 3) heteroatoms, wherein each heteroatom is independently the same or different and is N, O, S, or P.

"Substituted" means that the compound or group is substituted with at least one (e.g., 1, 2, 3, or 4) substituents instead of hydrogen, where each substituent is independently the same or different and is nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g, benzyl), $C_{7-12}$ alkylarylene (e.g, toluyl), $C_{4-12}$ heterocycloalkyl, $C_{3-12}$ heteroaryl, $C_{1-6}$ alkyl sulfonyl (—S(=O)$_2$—alkyl), $C_{6-12}$ arylsulfonyl (—S(=O)$_2$—aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

While the invention has been described with reference to an exemplary embodiment or embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof.

What is claimed is:

1. A color-reduced alkanolamine composition, the composition comprising:
   an alkanolamine; and
   from 5 to 30 wt. % of a borane complex of the formula L·BR$_a$H$_{3-a}$; wherein:
   L is ammonia;
   at least one R group is a $C_{1-12}$ alkyl group; and
   wherein a is 1 or 2;
   wherein the alkanolamine is a mono($C_{1-10}$ alkanol)amine, a di($C_{1-10}$ alkanol)amine, a tri($C_{1-10}$ alkanol)amine, an N-($C_{1-10}$ alkyl) di($C_{2-4}$ alkanol)amine, an N,N-di($C_{1-10}$ alkyl) ($C_{2-4}$ alkanol)amine, an N-($C_{1-10}$ alkanol)pyrrolidine, N-($C_{1-10}$ alkanol)imidazolidine, an N-($C_{1-10}$ alkanol)piperidine, an N-($C_{1-10}$ alkanol)piperazine or a combination comprising at least one of the foregoing.

2. The composition of claim 1, wherein the alkanolamine is a mono($C_{1-10}$ alkanol)amine.

3. The composition of claim 1, wherein the alkanolamine is a tri($C_{1-10}$ alkanol)amine.

4. The composition of claim 1, comprising less than 5 wt % of water based on the total weight of the alkanolamine.

5. A color-reduced alkanolamine composition, the composition comprising:
   an alkanolamine and from 5 to 30 wt. % of a borane complex based on the weight of the composition, wherein the composition has a Platinum-Cobalt Color Value, Test Method ASTM D1209, of less than 50, wherein:
   the borane complex is of the formula L·BR$_a$H$_{3-a}$ wherein L is ammonia and each R is a $C_{1-12}$ alkyl group, wherein a is 1 or 2.

6. A color-reduced alkanolamine composition, the composition comprising:
   an alkanolamine and from 5 to 30 wt. % of a borane complex of the formula L·BR$_a$H$_{3-a}$;
   wherein L is ammonia;
   wherein at least one R group is present and is selected from the group consisting of a $C_{1-12}$ alkyl group, a $C_{3-8}$ cycloalkyl group, a $C_{3-7}$ heterocycloalkyl group, a $C_{6-10}$ aromatic group and a $C_{3-15}$ heteroaromatic group; and
   wherein a is 1 or 2.

7. The composition of claim 6, wherein the at least one R group is a $C_{6-10}$ aromatic group.

8. The composition of claim 1, wherein the borane complex is present in an amount of from 10 to 30 wt. % by weight of the composition.

9. The composition of claim 1, wherein the borane complex is present in an amount of from 20 to 30 wt. % by weight of the composition.

10. The composition of claim 1, wherein borane complex comprises at least two R groups, wherein another of the at least two R groups is selected from the group consisting of a $C_{3-8}$ cycloalkyl group, a $C_{3-7}$ heterocycloalkyl group, a $C_{6-10}$ aromatic group and a $C_{3-15}$ heteroaromatic group.

* * * * *